(12) United States Patent
Soroka et al.

(10) Patent No.: US 9,772,094 B2
(45) Date of Patent: Sep. 26, 2017

(54) ILLUMINATOR

(71) Applicant: Sunoptic Technologies LLC, Jacksonville, FL (US)

(72) Inventors: Nicholas R. Soroka, Jacksonville, FL (US); Walter Orozco, Jacksonville, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 192 days.

(21) Appl. No.: 14/936,189

(22) Filed: Nov. 9, 2015

(65) Prior Publication Data
US 2017/0130940 A1    May 11, 2017

(51) Int. Cl.
| | |
|---|---|
| F21V 19/02 | (2006.01) |
| F21V 7/08 | (2006.01) |
| F21V 7/06 | (2006.01) |
| F21V 29/76 | (2015.01) |
| F21V 23/06 | (2006.01) |
| A61B 90/35 | (2016.01) |

(52) U.S. Cl.
CPC .............. *F21V 19/02* (2013.01); *A61B 90/35* (2016.02); *F21V 7/06* (2013.01); *F21V 7/08* (2013.01); *F21V 23/06* (2013.01); *F21V 29/76* (2015.01)

(58) Field of Classification Search
CPC ......... A61B 90/35; F21V 19/02; F21V 29/76; F21V 23/06
See application file for complete search history.

(56) References Cited

U.S. PATENT DOCUMENTS

| | | | |
|---|---|---|---|
| 5,295,052 | A | 3/1994 | Chin et al. |
| 5,329,436 | A | 7/1994 | Chiu |
| 5,961,203 | A | 10/1999 | Schuda |
| 6,123,437 | A | 9/2000 | Holmes |
| 7,018,073 | B2 | 3/2006 | Koegler et al. |
| 7,331,699 | B2 | 2/2008 | Gawalkiewicz et al. |
| 7,510,313 | B2 | 3/2009 | Blum et al. |
| 7,815,335 | B2 | 10/2010 | Frick |
| 2002/0018186 | A1 | 2/2002 | Sea-Huang et al. |

*Primary Examiner* — Andrew Coughlin
*Assistant Examiner* — Christopher E Dunay
(74) *Attorney, Agent, or Firm* — Howson & Howson LLP

(57) ABSTRACT

A lamp mounting system for an illuminator is provided. The lamp mounting system includes a framework assembly having separate, spaced-apart front and rear mounting components. The front and rear mounting components are movable relatively toward and away from each other between open and retracted positions. The lamp mounting system also includes a separate lamp module having opposite ends. The front and rear mounting components, in the retracted position, capture and suspend the lamp module therebetween in a manner ensuring proper alignment between the lamp module and collection optics.

16 Claims, 3 Drawing Sheets

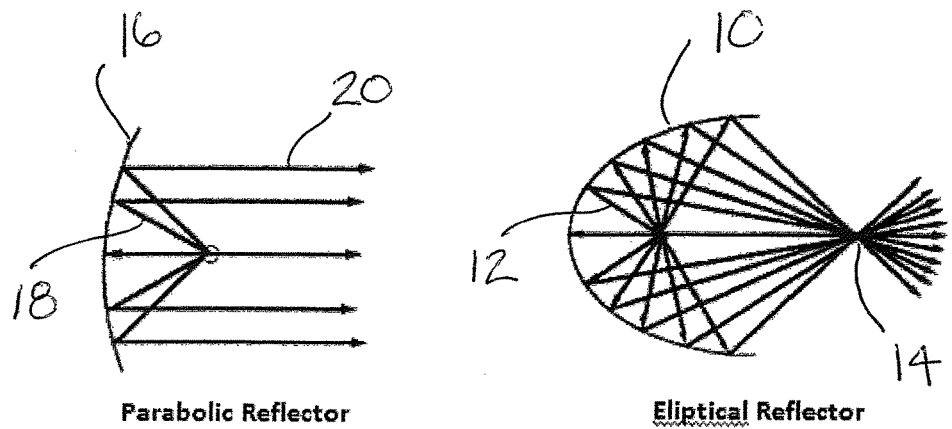
Parabolic Reflector
Fig. 2
Eliptical Reflector
Fig. 1
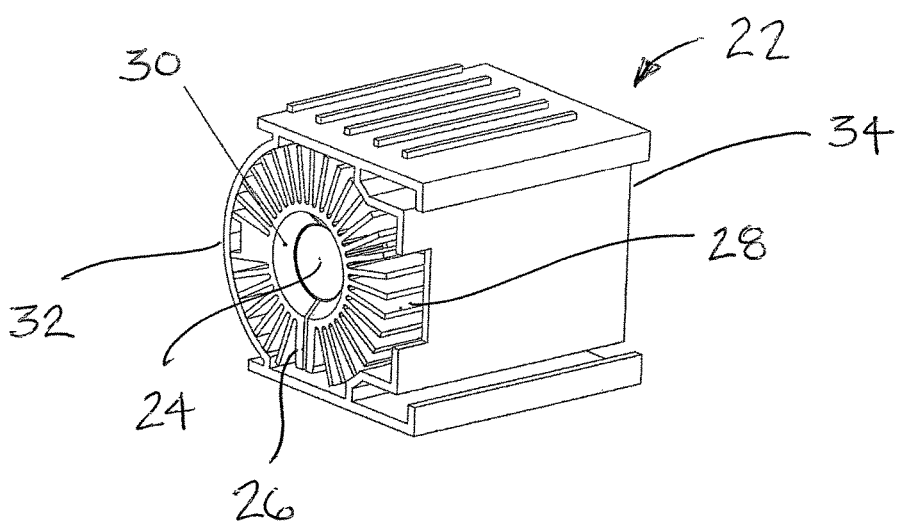
Fig. 3

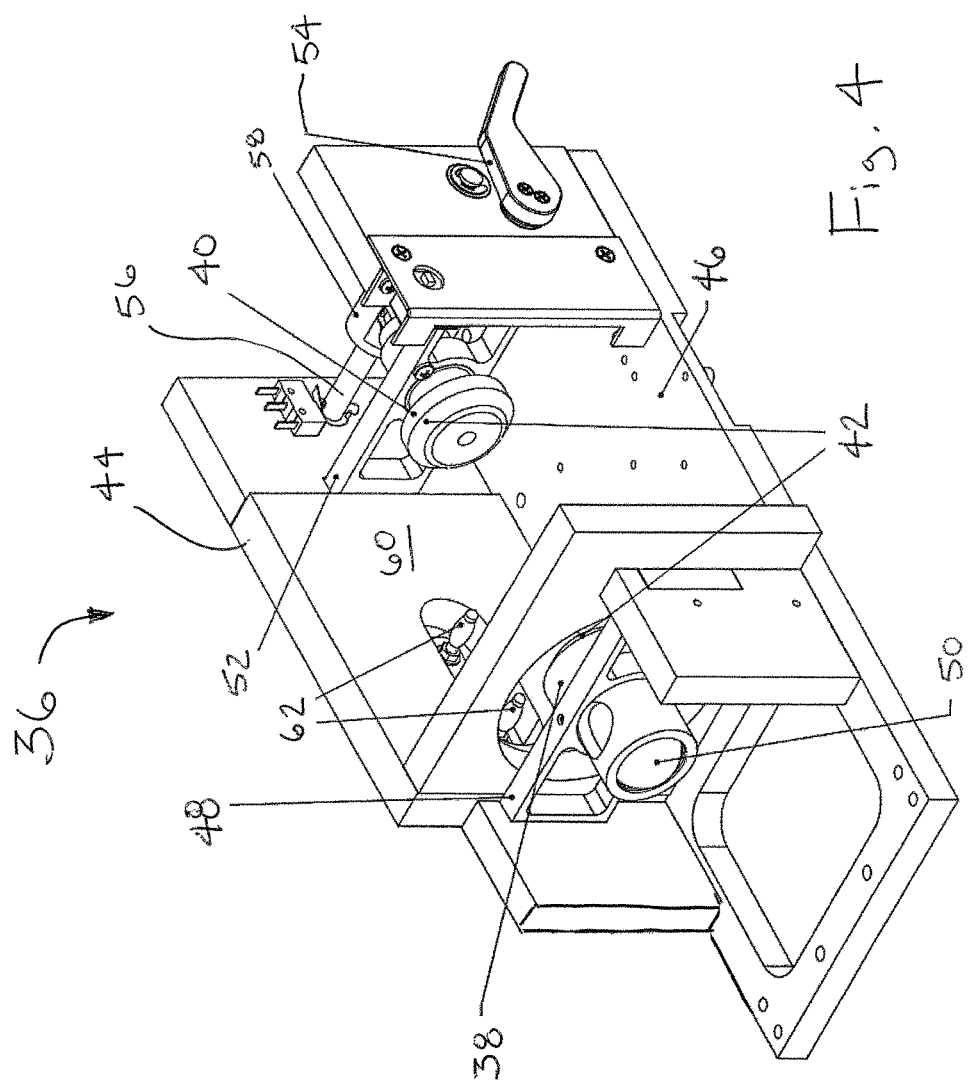

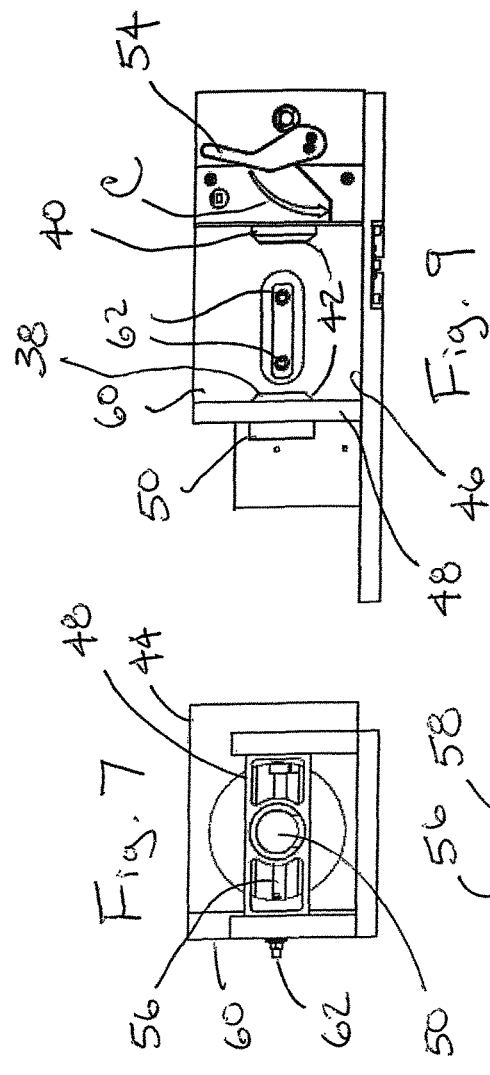
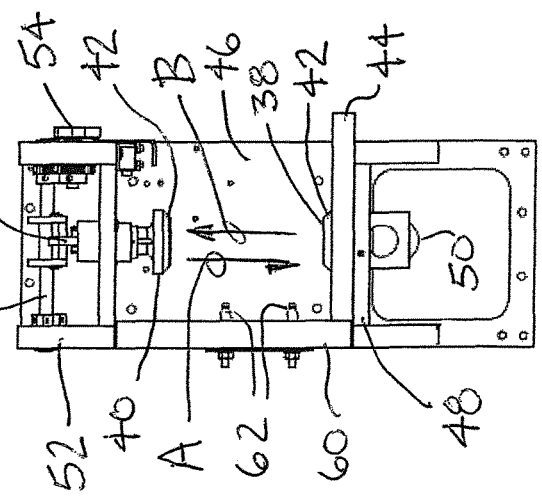
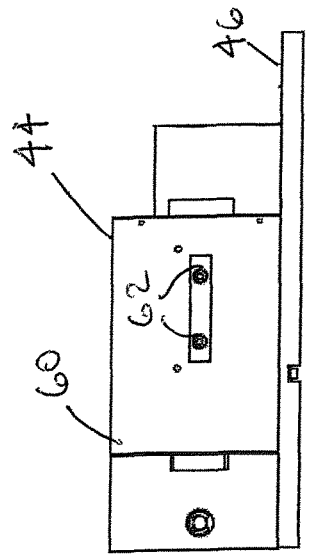
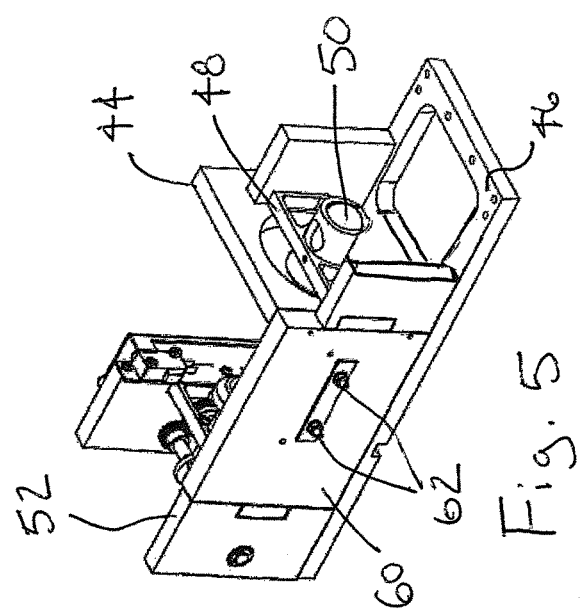

ILLUMINATOR

BACKGROUND

An illuminator, or light source, is provided for producing a high intensity light beam that may be used, for instance, for surgical site illumination or the like.

By way of example, a so-called fiberoptic illuminator or remote illumination device typically includes a lamp or light source within a housing and a jack or port providing a fiber optic cable interface that permits an end fitment or termination of a fiber optic bundle or cable to be connected to the housing so that a high intensity light beam may be directed and introduced into an end of the fiber optic bundle or cable. The cable may transmit the light to an endoscope, headlamp, or like medical/surgical device tethered to the illuminator.

An example of a lamp or light source that may be used in a remote illumination device is a xenon arc lamp. A xenon arc lamp is a specialized type of gas discharge lamp which produces light by passing electricity through ionized xenon gas at high pressure. Such a lamp produces bright white light that closely mimics natural sunlight. Of course, other types of lamps are also utilized.

BRIEF DESCRIPTION OF THE DRAWINGS

The features and advantages of embodiments disclosed herein should become apparent from the following description when taken in conjunction with the accompanying drawings, in which:

FIG. 1 is a view of an ellipsoidal-shaped reflector according to an embodiment.

FIG. 2 is a view of a parabolic reflector according to an embodiment.

FIG. 3 is a perspective view of a lamp and heatsink assembly according to an embodiment.

FIG. 4 is a perspective view of a lamp mounting system for an illuminator according to an embodiment.

FIG. 5 is a perspective view of an opposite side of the lamp mounting system of FIG. 4.

FIG. 6 is a top plan view of the lamp mounting system of FIG. 4.

FIG. 7 is a front elevational view of the lamp mounting system of FIG. 4.

FIG. 8 is a left side elevational view of the lamp mounting system of FIG. 4.

FIG. 9 is a right side elevational view of the lamp mounting system of FIG. 4.

DETAILED DESCRIPTION

Although not otherwise shown in the drawings, an illuminator will typically include an exterior housing or enclosure in which a lamp is contained and mounted. The enclosure may be provided in a generally-rectangular, box-shaped configuration. Of course, other housing shapes and configurations can be utilized and may be provided in a manner such that the illuminator is of a relatively small size occupying only a relatively small amount of space in an operating room or like environment. According to at least some embodiments, the illuminator may be constructed to provide a source of light of great intensity, to operate at low noise, and to be able to accommodate internal heat management issues even after hours of continuous operation of the illuminator.

Illuminators that utilize xenon arc lamps and like light sources may include a reflector and collection optics. For instance, a xenon arc-lamp used for surgical site illumination may be used with a reflector that focuses light into a pin-pointed area ("focal point") or a reflector that collimates light (i.e., arranges rays of light in parallel). By way of example, FIG. 1 illustrates the physics of an ellipsoidal-shaped-reflector 10 that focuses light 12 into a pin-pointed area 14, and FIG. 2 illustrates a parabolic-shaped reflector 16 that collimates light 18 thereby forming a plurality of parallel light rays 20.

A difficulty in mounting lamps and reflectors in illuminators is the need to assure precise alignment of the lamp body relative to the reflector and collection optics such that, for instance, a focal point of luminous lux is precisely coupled into the light-receiving lenses and/or fibers for transmission to a surgical site or the like. Thus, an alignment mechanism is needed to precisely position the collection optics at the lamp focal-point (such as at area 14 in FIG. 1) or other desired location. Preferably, such an alignment mechanism should not require high mechanical aptitude of a user, such as when removing and replacing lamps and reconnecting the alignment mechanism.

Accordingly, embodiments disclosed herein are directed to a non-interfering focusing and coupling device that saves operators time and greatly simplifies the task of replacing lamp modules in illuminators where a lamp and reflector combination are employed. The embodiments disclosed herein assure that the alignment of a lamp/reflector combination with collection optics can be replicated, for instance, when a spent lamp is required to be replaced with a new lamp in a manner requiring a minimum of training and skill.

A lamp module or assembly 22 including a xenon arc lamp 24 and reflector (not shown) surrounded by a heatsink 26 is shown in FIG. 3. The lamp 24 may be any type of light source, and the reflector may be an elliptical, parabolic, or other type of reflector. The heatsink 26 encapsulates the lamp 24 and reflector and includes a plurality of vanes 28 for transferring and dissipating heat generated by the lamp 24 during use. For example, the illuminator may include a fan (not shown) for causing a flow of ambient air to flow across, along, or through the heatsink 26 for cooling the heatsink. The heatsink 26 may be made of metal or a like heat conducting material.

A countersink 30 is formed and/or machined into the front and rear end faces of the module or assembly 22. For instance, countersinks 30 may be formed in the heatsink 26 and positioned adjacent the front and rear ends of the lamp module 22. FIG. 3 shows the countersink 30 adjacent the front end 32 of the lamp module 22. A similar countersink (not shown) is formed adjacent the opposite (rear) end 34 of the assembly 22 and may be aligned with countersink 30.

A lamp mounting system 36 for mounting the separate lamp module 22 within an illuminator is shown in FIGS. 4-9. The mounting system 36 is configured to suspend the lamp module 22 (including a reflector) between two electrically-insulated mounting components, such as front and rear mounting cones, 38 and 40, as best shown in FIG. 5. The front and rear mounting cones, 38 and 40, may be made of electrically-insulated and thermally stable material, such as a ceramic material or the like. The rear mounting cone 40 may be generally solid for engaging the rear end 34 of the lamp module 22 since light is not required to pass through the rear mounting cone 38. However, the front mounting cone 40 may be annular or hollow and have a center opening or the like that permits light emitted from the front end 32 of the lamp module 22 to be transmitted therethrough.

The front and rear mounting cones, 38 and 40, are shaped and sized to fit within and stably engage the countersinks 30 formed in the front and rear ends, 32 and 34, of the lamp module 22. For instance, each of the front and rear mounting cones, 38 and 40, may have a frustoconical-shaped surface 42 that is received within and mates with one of the countersinks 30. In this manner, the lamp module 22 may be captured and suspended in a stable condition between the front and rear mounting cones, 38 and 40.

To enable placement or removal of the lamp module 22 relative to the front and rear mounting cones, 38 and 40, the front and rear mounting cones, 38 and 40, are moveable relative to each other into a retracted or closed position in which the lamp module 22 may be clamped and suspended therebetween and an extended or open position in which the lamp module 22 is free to be removed from or placed between the front and rear mounting cones, 38 and 40. This permits ease of removal of a spent lamp and replacement of a new lamp in a manner that ensures proper alignment of the lamp/reflector with the fixed collection optics of the illuminator without any need to connect any special collection optic mounting systems to the lamp body.

The lamp mounting system 36 may include a framework assembly 44 for interconnecting the front and rear mounting cones, 38 and 40. For instance, the framework assembly 44 may include a platform or base 46 upon which the lamp module 22 may be rested when inserted into the illuminator between the front and rear mounting cones, 38 and 40, when the mounting cones are in an open position as shown. The framework assembly 44 may also include front framework 48 for securing a collection optic 50 in a fixed position in front of the front mounting cone 38 to properly collect light emitted from the lamp module 22 when the lamp module 22 is properly engaged and pinned against the front mounting cone 38.

For example, the collection optic 50 may be aligned relative to the lamp and an elliptical reflector of the lamp module 22 such as to focus the luminous flux into other optic components (not shown) forward of the collection optic 50 for delivery of the light to a surgical site or the like. Thus, provided the front mounting cone 38 is positioned within the countersink 30 formed in the front end 32 of the lamp module 22, proper alignment is automatically provided to maximize light transmission.

For purposes of forcing and holding the lamp module 22 against the front mounting cone 38, the framework assembly 44 may include rear framework 52 that supports the rear mounting cone 40 in a manner that permits the rear mounting cone 40 to be moved in a forward direction "A" (see FIG. 6) toward the front mounting cone 38 or a rearward direction "B" (see FIG. 6) away from the front mounting cone 38 thereby adjusting the distance between the front and rear mounting cones, 38 and 40. Of course, the illustrated configuration may be reversed such that the front mounting cone is caused to move relative to a stationary rear mounting cone, or both the front and rear mounting cones may be movable.

In the illustrated embodiment, the rear framework 52 may include a lever 54 or like device for causing rotation of a rod 56 that is connected to the rear mounting cone 40 via a linkage 58. The linkage 58 is configured to cause the rear mounting cone 40 to move forward or rearward (see directions "A" and "B" in FIG. 6) relative to the front mounting cone 40 when the lever 54 is pivoted thereby causing the rod 56 to rotate.

In FIG. 9, the level 54 may be positioned such that the rear mounting cone 40 is located in a rearward position. However, movement of the lever 54 in a counter-clockwise direction as shown by arrow "C" in FIG. 9 may cause the rear mounting cone 40 to move forward, engage the countersink 30 formed in the rear end 34 of the lamp module 22 and automatically lift the lamp module 22 upward so that the lamp module 22 is clamped between and suspended by the front and rear mounting cones, 38 and 40.

The framework assembly 44 may also include a sidewall 60 on which so-called floating banana plugs or electric connectors 62 are mounted. The plugs 62 are positioned to automatically engage the lamp electrical lugs (not shown) of the lamp module 22 to power leads from the ballast of the illuminator.

Accordingly, the lamp mounting system 36 may be included within the housing of an illuminator. The lever 54 may be positioned such that the front and rear mounting cones, 38 and 40, are in an open position thereby enabling an old and/or spent lamp module 22 to be readily removed from the illuminator. A new lamp module 22 may then be inserted between the front and rear mounting cones, 38 and 40. Thereafter, the lever 54 may be actuated such as to cause the rear mounting cone 40 to move toward the front mounting cone 38. This causes engagement of the front and rear mounting cones, 38 and 40, with the corresponding countersinks 30 formed in the opposite ends, 32 and 34, of the lamp module 22. This engagement lifts the lamp module 22 off the base 46 of the framework assembly 44 and results in the lamp module 22 being suspended solely by and clamped between the front and rear mounting cones, 38 and 40. The front end 32 of the lamp module 22 is thereby pinned against the front mounting cone 38 and this ensures that the lamp/reflector of the lamp module 22 are properly aligned relative to the collection optic 50. This alignment is able to be achieved repeatedly after every change of lamp modules 22 and requires only a minimum of skill by the operator.

While preferred embodiments of illuminators, lamp modules, and lamp mounting systems have been described in detail, various modifications, alternations, and changes may be made without departing from the spirit and scope of the light engines according to the present invention as defined in the appended claims.

We claim:

1. A lamp mounting system for an illuminator, comprising:
    a framework assembly including separate spaced-apart front and rear mounting components, said front and rear mounting components being movable relatively toward and away from each other on said framework assembly between a retracted position and an open position; and
    a separate lamp module having opposite ends;
    said front and rear mounting components capturing and suspending said lamp module therebetween when said front and rear mounting components are moved to said retracted position; and
    said front and rear mounting components being sufficiently spaced apart when in said open position to enable removal and replacement of said lamp module relative to said framework assembly,
    wherein said lamp module includes a lamp and a reflector,
    further comprising a collection optic mounted on said framework assembly in front of said front mounting component, and
    wherein when said lamp module is captured and suspended between said front and rear mounting components in said retracted position, said collection optic is automatically properly aligned with said lamp and reflector of said lamp module to maximize light transmission.

2. The lamp mounting system according to claim 1, wherein said opposite ends of said lamp module have surfaces that are engaged by and mated to cooperating surfaces on said front and rear mounting components to enable said lamp module to be securely and stably suspended between said front and rear mounting components when said front and rear mounting components are in said retracted position.

3. The lamp mounting system according to claim 2, wherein said surface on at least one of said opposite ends of said lamp module is in the form of a countersink.

4. The lamp mounting system according to claim 3, wherein a shape of said cooperating surface on at least one of said front and rear mounting components is frustoconical.

5. The lamp mounting system according to claim 1, wherein said reflector is an ellipsoidal-shaped reflector and said collection optic is automatically properly aligned with a focal point of light produced by said lamp and reflected by said reflector.

6. The lamp mounting system according to claim 1, wherein said reflector is a parabolic reflector for collimating light produced by said lamp and collimated by said reflector.

7. The lamp mounting system according to claim 1, wherein said lamp is a xenon arc lamp.

8. The lamp mounting system according to claim 1, wherein said lamp module includes a heatsink having a plurality of heat-dissipating fins surrounding said lamp and reflector.

9. The lamp mounting system according to claim 1, further comprising at least one floating electric connector mounted to said framework assembly that automatically forms an electric connection to said lamp when said lamp module is captured and suspended between said front and rear mounting components.

10. The lamp mounting system according to claim 1, wherein said framework assembly includes a lever for mechanically causing said rear mounting component to move relative to said front mounting component in directions toward and away from said front mounting component.

11. The lamp mounting system according to claim 10, wherein said framework assembly includes a linkage that causes said rear mounting component to move toward or away from said front mounting component when said level is caused to pivot.

12. The lamp mounting system according to claim 1, wherein said front and rear mounting components are made of electrically-insulating, thermally-stable material.

13. The lamp mounting system according to claim 12, wherein said front mounting component is annular and has a central opening for permitting light emitted by said lamp module to be transmitted through said front mounting component.

14. An illuminator, comprising:
a lamp module including a lamp and a parabolic or elliptical reflector contained within a heatsink having heat-dissipating fins, said lamp module having front and rear ends each having a countersink formed therein;
a framework assembly including framework on which separate front and rear mounting components are mounted in a spaced-apart relation for receiving said lamp module therebetween, said front and rear mounting components including surfaces cooperatively receivable within said countersinks; and
a mechanism for causing relative movement of said rear mounting component away from said front mounting component to enable said lamp module to be removed from said framework assembly or placed freely on said framework assembly and for causing relative movement of said rear mounting component toward said front mounting component to enable said lamp module to be lifted off said framework assembly and suspended by and between said front and rear mounting components,
a collection optic mounted on said framework assembly in front of said front mounting component, and wherein when said lamp module is captured and suspended between said front and rear mounting components, said collection optic is automatically properly aligned with a focal point of light produced by said lamp and reflected by said reflector.

15. The illuminator according to claim 1, wherein said lamp is a xenon arc lamp.

16. The lamp mounting system according to claim 15, further comprising a pair of floating electric connectors mounted to said framework assembly that automatically form an electric connection to said lamp when said lamp module is captured and suspended between said front and rear mounting components.

* * * * *